United States Patent [19]

Inomata et al.

[11] Patent Number: 5,200,543
[45] Date of Patent: Apr. 6, 1993

[54] SILOXANE COMPOUNDS

[75] Inventors: Hiroshi Inomata; Hiromasa Yamaguchi; Kenichi Fukuda, all of Annaka, Japan

[73] Assignee: Shin-Etsu Chemical Co., Ltd., Tokyo, Japan

[21] Appl. No.: 906,835

[22] Filed: Jul. 2, 1992

[30] Foreign Application Priority Data

Jul. 4, 1991 [JP] Japan .................................. 3-190767

[51] Int. Cl.$^5$ ................................................ C07F 7/08
[52] U.S. Cl. ...................................... 556/434; 549/215
[58] Field of Search ......................... 556/434; 549/215

[56] References Cited

U.S. PATENT DOCUMENTS 2,884,434  4/1959  Smith .................................. 556/434

FOREIGN PATENT DOCUMENTS 0465263  1/1992  European Pat. Off. ............. 556/434
1-236282  9/1989  Japan .

Primary Examiner—Paul F. Shaver
Attorney, Agent, or Firm—Millen, White, Zelano & Branigan

[57] ABSTRACT

Novel siloxane compounds containing a SiH group, an alkoxy or epoxy group-containing organic group attached to a silicon atom, and a perfluoropolyether group-containing organic group, each at least one per molecule, are useful tackifiers for imparting good adhesion to various resins and even fluorinated silicone resins.

4 Claims, 2 Drawing Sheets

SILOXANE COMPOUNDS

This invention relates to novel siloxane compounds useful in imparting good adhesion to silicone resins so that the silicone resins well adhere to various articles, and more particularly, to siloxane compounds having a fluorinated group useful in imparting good adhesion to fluorinated silicone resins.

BACKGROUND OF THE INVENTION

It is a common practice in the prior art to blend siloxane compounds with silicone resins for imparting adhesion to the silicone resins. For example, Japanese Patent Publication No. 236282/1989 discloses siloxane compounds having an alkoxy and/or epoxy group-containing organic group attached to a silicon atom and a SiH group in a molecule. Although these siloxane compounds perform well for ordinary silicone resins, they impart less satisfactory adhesion to fluorinated silicone resins. It is thus desired to develop siloxane compounds capable of imparting good adhesion to fluorinated silicone resins.

Therefore, an object of the present invention is to provide novel and improved siloxane compounds which have good affinity to fluorinated silicone resins and significantly contribute to solvent resistance and low moisture permeability.

SUMMARY OF THE INVENTION

According to the present invention, there is provided a novel siloxane compound of the general formula (1).

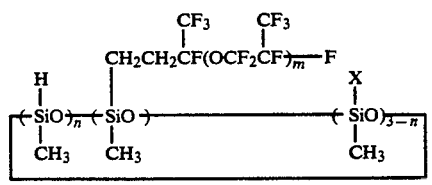

In formula (1), X is a group of the following formula (2) or (3), m is an integer of 1 to 4, and n is equal to 1 or 2.

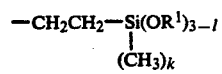

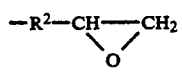

In formulae (2) and (3), $R^1$ is a monovalent hydrocarbon group, $R^2$ is a divalent organic group, and k is an integer of 0 to 2.

We have succeeded in preparing the siloxane compound of formula (1) by carrying out an addition reaction between an organohydrogen-siloxane of the following formula (4) and a perfluoropolyether having an aliphatic double bond of the following formula (5) and adding one or two molecules of an alkoxy group-containing silicon compound or epoxy group-containing compound to one molecule of the reaction product.

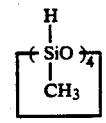

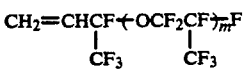

As seen from formula (1), these siloxane compounds contain a hydrogen atom attached to a silicon atom (SiH group) capable of reacting with silicone resins, an alkoxy or epoxy group-containing organic group attached to a silicon atom participating in adhesion to substrates or articles, and a perfluoropolyether group-containing organic group, each at least one per molecule. The siloxane compounds of formula (1) are found to have good affinity to fluorinated silicone resins and significantly contribute to solvent resistance and low moisture permeability. Therefore, the siloxane compounds are useful tackifiers capable of imparting good adhesion to fluorinated silicone resins.

BRIEF DESCRIPTION OF THE ACCOMPANYING DRAWINGS

DETAILED DESCRIPTION OF THE INVENTION

Figure 1:
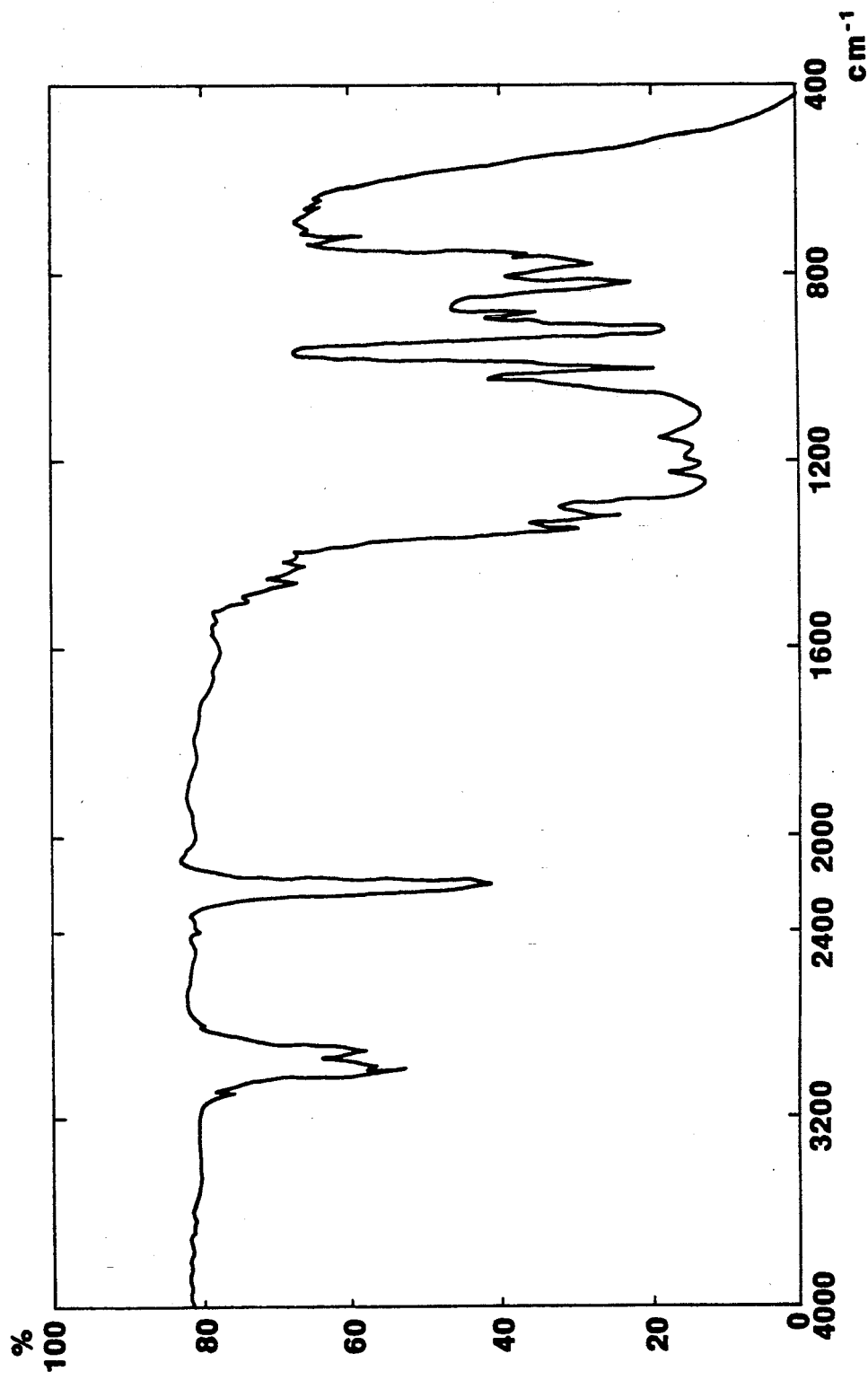
FIG. 1 is an IR absorption spectrum of the siloxane compound obtained in Example 1.

According to the present invention, the siloxane compounds are of formula (1).

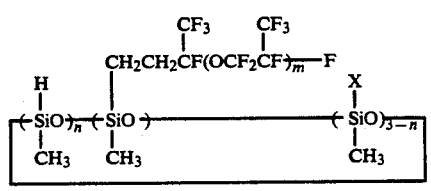

In formula (1), X is a group of the following formula (2) or (3), m is an integer of 1 to 4, and n is equal to 1 or 2.

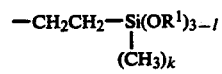

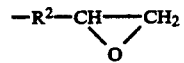

In formulae (2) and (3), $R^1$ is a monovalent hydrocarbon group, $R^2$ is a divalent organic group, and k is an integer of 0 to 2.

In formula (2), $R^1$ is a monovalent hydrocarbon group which is not particularly limited, for example, a lower alkyl group such as methyl and ethyl, and k is an integer of 0 to 2. In formula (3), $R^2$ is a divalent organic group which is not particularly limited, for example, a lower alkylene group which may have an oxygen atom at the end or at an intermediate, such as $-(CH_2)_4-$, $-(CH_2)_2OCH_2-$, $-CH_2CH_2-$, $-(CH_2)_3O-$, and $-(CH_2)_3OCH_2-$.

In formula (1), n is equal to 1 or 2, which means that the siloxane compound of the invention contains one or two hydrogen atoms each attached to a silicon atom, that is, one or two SiH groups and one or two alkoxy or epoxy group-containing organic groups each attached to a silicon atom in a molecule. Letter m associated with the perfluoropolyether group-containing organic group is an integer of 1 to 4 because of ease of synthesis. It is this perfluoropolyether group-containing organic group that provides affinity to fluorinated silicone resins and fluorinated rubbers.

The siloxane compound of formula (1) can be synthesized, for example, by carrying out an addition reaction between a SiH bond of an organohydrogensiloxane and an aliphatic double bond of a perfluoropolyether having such a bond in the presence of a platinum catalyst and adding an alkoxy group-containing silicon compound or epoxy group-containing compound to the reaction product in a similar addition reaction manner.

One of the starting reactants is an organohydrogensiloxane which is preferably of the following formula (4).

$$\left[\begin{array}{c}H\\|\\(SiO)_4\\|\\CH_3\end{array}\right] \quad (4)$$

The other starting reactant is a perfluoropolyether having an aliphatic double bond which is preferably of the following formula (5):

$$CH_2=CHCF-(OCF_2CF)_m-F \quad (5)$$
$$\quad\quad\quad |\quad\quad\quad\quad |$$
$$\quad\quad\quad CF_3\quad\quad\quad CF_3$$

wherein m is an integer of 1 to 4.

The addition reaction between the organohydrogensiloxane of formula (4) and the perfluoropolyether having an aliphatic double bond of formula (5) may be carried out in accordance with conventional methods using well-known addition reaction catalysts.

An alkoxysilyl or epoxy group may then be introduced into the addition reaction product in accordance with conventional methods using alkoxy group-containing silicon compounds such as vinyltrimethoxysilane or aliphatic unsaturated group-containing epoxy compounds.

EXAMPLE

Examples of the present invention are given below by way of illustration and not by way of limitation.

EXAMPLE 1

A 2-liter autoclave was charged with 600 grams (2.5 mol) of the compound of formula (4), 1195 grams (2.5 mol) of the compound of formula (6), and 4.8 grams of a 2-ethylhexanol modified platinum catalyst having a platinum concentration of 2% (Pt: $5.0\times 10^{-4}$ mol). The mixture was agitated for 7 hours at 150° C.

The reaction mixture was combined with 4.8 grams of 2-benzothiazolyldisulfide as a deactivator for the platinum catalyst and subjected to vacuum flash distillation and then vacuum distillation, obtaining a fluorinated siloxane of formula (7) as a fraction at 102°–104° C./9 mmHg.

$$\left[\begin{array}{c}H\\|\\(SiO)_4\\|\\CH_3\end{array}\right] \quad (4)$$

$$CH=CHCF-(OCF_2CF)_2-F \quad (6)$$
$$\quad\quad\quad |\quad\quad\quad\quad |$$
$$\quad\quad\quad CF_3\quad\quad\quad CF_3$$

$$\left[\begin{array}{cc}H & CH_2CH_2CF(OCF_2CF)_2F\\|&\quad\quad\quad |\quad\quad\quad\quad|\\(SiO)_3 & (SiO)\quad\quad CF_3\quad CF_3\\|&|\\CH_3 & CH_3\end{array}\right] \quad (7)$$

Next, a three-necked flask equipped with a condenser and thermometer was charged with 60 grams (0.84 mol) of the fluorinated siloxane and 30 grams of toluene and heated to 75° to 80° C. With thoroughly stirring, 1.000 grams of a toluene solution containing 0.082 grams of 2-ethylhexanol modified platinum catalyst having a platinum concentration of 2% (Pt: $8.4\times 10^{-6}$ mol) was added dropwise to the flask, and 24.5 grams of a toluene solution containing 9.5 grams (0.084 mol) of allylglycidyl ether was further added dropwise over 2.5 hours.

The reaction mixture was allowed to cool, combined with 0.082 grams of 2-benzothiazolyldisulfide, and then subjected to vacuum distillation, obtaining 33 grams (yield 47%) of a siloxane compound as a fraction at 167°–171° C./3 mmHg. Based on the following analytical data, the compound was found to have the structure of the following formula (8).

$$\left[\begin{array}{ccc}H & CF_3\quad CF_3 & O\\|&|\quad\quad|& /\backslash\\SiO)_2\;(SiO) & CH_2CH_2CFOCF_2CFOCF_2CF_2CF_3 \; CH_2CH_2CH_2OCH_2CHCH_2 & (SiO)\\|&|&|\\CH_3 & CH_3 & CH_3\end{array}\right] \quad (8)$$

Elemental analysis:

|  | C | H | Si | F |
|---|---|---|---|---|
| Calcd.* (%) | 28.85 | 3.51 | 13.49 | 38.78 |
| Found (%) | 28.73 | 3.84 | 12.84 | 39.35 |

*calculated as $C_{20}H_{29}O_3F_{17}Si_4$

GCMS: 832 (M+)
IR absorption spectrum:

The compound gave an IR spectrum as shown in FIG. 1. There were observed a characteristic absorption peak attributable to a SiH group at a wave number of 2170 cm$^{-1}$ and a characteristic absorption peak attributable to an epoxy group (C—H) at a wave number of 3000–3100 cm$^{-1}$, SiH amount:

Calcd.: 0.0024 mol/g  Found: 0.0026 mol/g

Epoxy equivalent: Calcd.: 832 g/mol Found: 970 g/mol $^1$H-NMR spectrum: relative to TMS.
δ=4.67 ppm, (—SiH, bs, 2H),
δ=0.17 ppm, (—SiCH$_3$, bs, 12H),
δ=0.43 to 1.00 ppm (Si—CH$_2$—C, m, 4H),
δ=1.87 to 2.30 ppm (CF—CH$_2$—C, m, 2H),
δ=1.30 to 1.80 ppm (C—CH$_2$—C, m, 2H),
δ=3.10 to 3.60 ppm (C—CH$_2$—O, m, 4H),

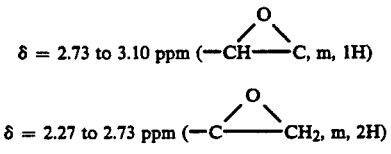

$^{19}$F-NMR spectrum: relative to CF$_3$COOH
φ=—1.77 to —4.4 ppm, (C—CF$_3$, —CF$_2$—O—, m, 13F),
φ=—50.6 ppm (CH$_2$—CF—, m, 1F),
φ=—51.0 ppm (—C—CF$_2$—C—, s, 2F),
φ=—66.2 ppm (C—CF—C, m, 1F).

EXAMPLE 2

The procedure of Example 1 was repeated except that 12.4 grams (0.084 mol) of vinyltrimethoxysilane was used instead of 9.5 grams (0.084 mol) of allylglycidyl ether. There was obtained a siloxane compound as a fraction at 145°-149° C. Based on the following analytical data, the compound was found to have the structure of the following formula (9).

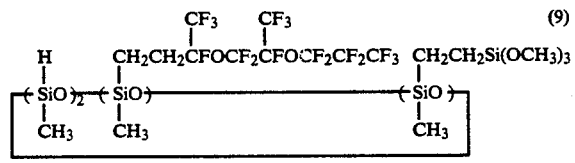

Elemental analysis:

|            | C     | H    | Si    | F     |
|------------|-------|------|-------|-------|
| Calcd.* (%) | 26.33 | 3.60 | 16.20 | 37.26 |
| Found (%)  | 26.74 | 3.42 | 15.41 | 37.86 |

*calculated as C$_{19}$H$_{31}$O$_9$F$_{17}$Si$_5$

Figure 2:
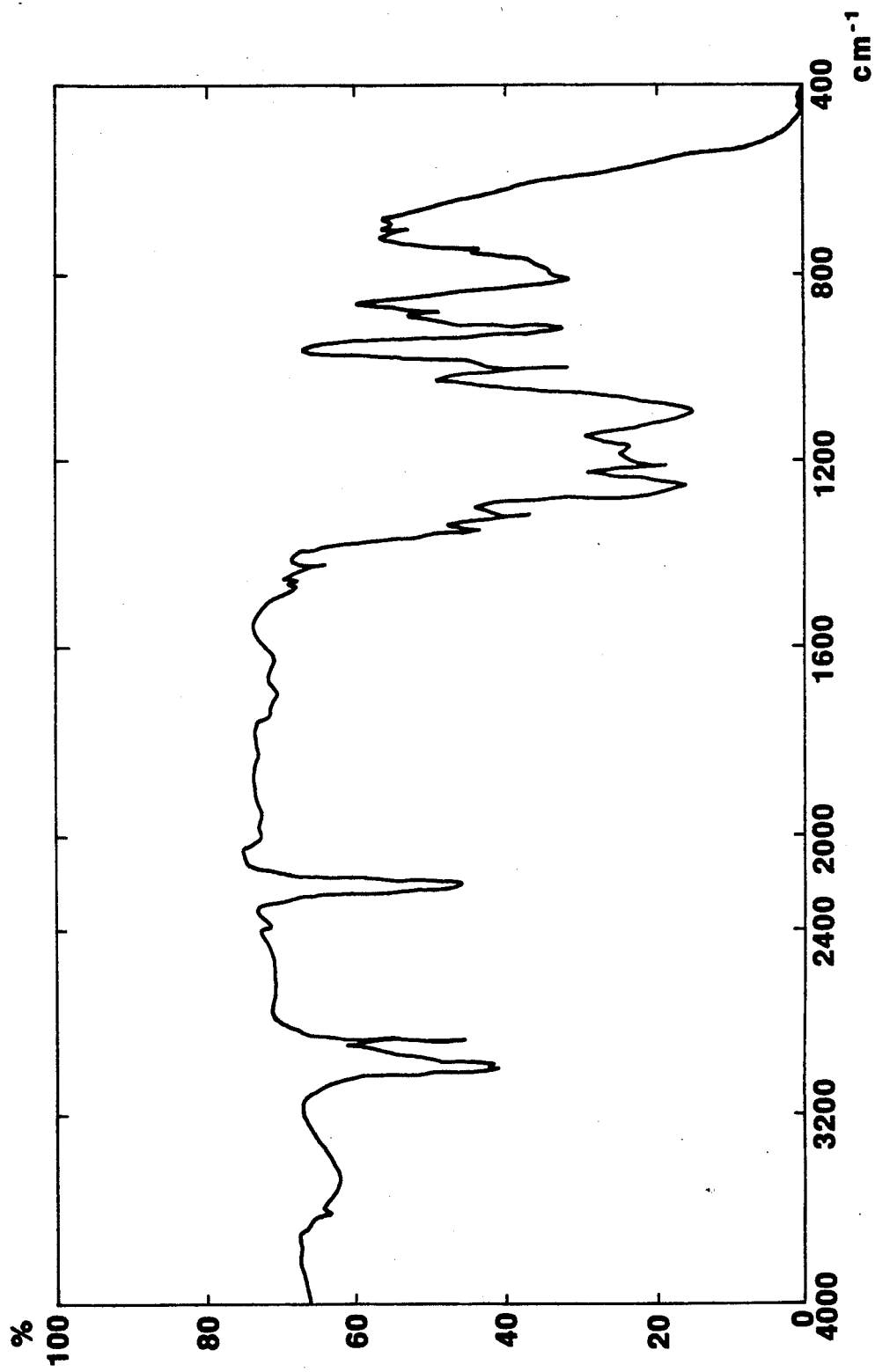
FIG. 2 is an IR absorption spectrum of the siloxane compound obtained in Example 2.

GCMS: 866 (M+).
IR absorption spectrum:
The compound gave an IR spectrum as shown in FIG. 2. There were observed a characteristic absorption peak attributable to a SiH group at a wave number of 2170 cm$^{-1}$ and a characteristic absorption peak attributable to SiOCH$_3$ at a wave number of 2850 cm$^{-1}$.
SiH amount:
Calcd.: 0.0023 mol/g Found: 0.0021 mol/g
$^1$H-NMR spectrum: relative to TMS,
δ=4.73 ppm (SiH, bs, 2H)
δ=0.20 ppm (SiCH$_3$, m, 12H)
δ=0.50 to 1.20 ppm (Si—CH$_2$—C, m, 6H)
δ=1.87 to 2.53 ppm (C—CH$_2$—C, m, 2H)
δ=3.53 ppm (O—CH$_3$, s, 9H)
$^{19}$F-NMR spectrum: relative to CF$_3$COOH,
φ=—2.8 to —5.6 ppm, (C—CF$_2$, CF$_2$—O—, m, 13F),
φ=—51.4 ppm (CH$_2$—CF—, m, 1F),
φ=—52.1 ppm (C—CF$_2$—C—, s, 2F),
φ=—67.1 ppm (C—CF—C, m, 1F).

There have been described siloxane compounds which are effective for imparting adhesion and thus useful tackifiers for various resins including fluorinated silicone resins. Due to the presence of a fluorinated group, the siloxane compounds have high affinity to fluorinated silicone resins so that the siloxane compounds can be blended with such resins for imparting good adhesion thereto while providing solvent resistance and low humidity permeability.

Although some preferred embodiments have been described, many modifications and variations may be made thereto in the light of the above teachings. It is therefore to be understood that within the scope of the appended claims, the invention may be practiced otherwise than an specifically described.

We claim:
1. A siloxane compound of the formulae (1):

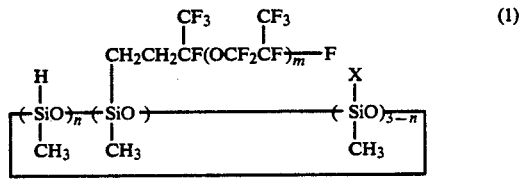

wherein
X is a group of the following formula (2) or (3):

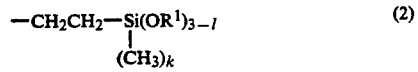

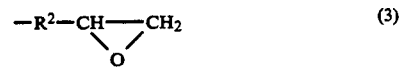

wherein
R$^1$ is a monovalent hydrocarbon group, R$^2$ is a divalent organic group, and k is an integer of 0 to 2, m is an integer of 1 to 4, and n is equal to 1 or 2.

2. The siloxane compound of claim 1 wherein X is a group of formula (2) wherein R$^1$ is a lower alkyl group.

3. The siloxane compound of claim 1 wherein X is a group of formula (3) wherein R$^2$ is a lower alkylene group which may contain an oxygen atom.

4. The siloxane compound of claim 1, wherein X is a group of formula (3) and R$^2$ is selected from the group consisting of —(CH$_2$)$_4$—, —(CH$_2$)$_2$OCH$_2$—, —CH$_2$CH$_2$—, —(CH$_2$)$_3$O— and —(CH$_2$)$_3$OCH$_2$—.

* * * * *